United States Patent [19]

Shennib

[11] Patent Number: 5,197,332
[45] Date of Patent: Mar. 30, 1993

[54] HEADSET HEARING TESTER AND HEARING AID PROGRAMMER

[75] Inventor: Adnan A. Shennib, Fremont, Calif.

[73] Assignee: CalMed Technology, Inc., Union City, Calif.

[21] Appl. No.: 838,542

[22] Filed: Feb. 19, 1992

[51] Int. Cl.⁵ .................................................. A61B 1/22
[52] U.S. Cl. ....................................... 73/585; 128/746
[58] Field of Search .................... 73/585; 128/746, 903

[56] References Cited

U.S. PATENT DOCUMENTS

| | | | |
|---|---|---|---|
| 3,091,234 | 5/1963 | Jerger | 73/585 |
| 4,038,496 | 7/1977 | Feezor | 73/585 |
| 4,157,456 | 6/1979 | Voss | 73/585 |
| 4,284,847 | 8/1981 | Besserman | 73/585 |
| 4,489,610 | 12/1984 | Slavin | 73/585 |
| 4,759,070 | 7/1988 | Voroba et al. | 381/60 |
| 4,953,112 | 8/1990 | Widin et al. | 73/585 |
| 4,961,230 | 10/1990 | Rising | 381/69.2 |
| 4,964,304 | 10/1990 | Eckstein | 73/585 |
| 4,989,251 | 1/1991 | Mangold | 381/68.2 |

FOREIGN PATENT DOCUMENTS

| | | | |
|---|---|---|---|
| 2907842 | 9/1980 | Fed. Rep. of Germany | 73/585 |
| 3517749 | 11/1986 | Fed. Rep. of Germany | 73/585 |

*Primary Examiner*—Tom Noland
*Assistant Examiner*—Rose M. Finley
*Attorney, Agent, or Firm*—Schneck & McHugh

[57] ABSTRACT

A headset-based hearing tester and hearing aid programming instrument featuring an electronic module shaped as a headband having a connected acoustic transducer module. The electronic module includes microcontroller, internal and plug-in external memory for storage of program code and patient data. The headset instrument in conjunction with a hand-held patient response device is capable of automatic hearing testing. The produced audio stimuli including test tones, speech and verbal instructions are retrieved from external memory cards. The instrument automatically computes fitting parameters and is capable of programming a programmable hearing aid via a port for direct wire programming or via wireless methods including inductive coil coupling to a hearing aid equipped with a receiving coil.

19 Claims, 7 Drawing Sheets

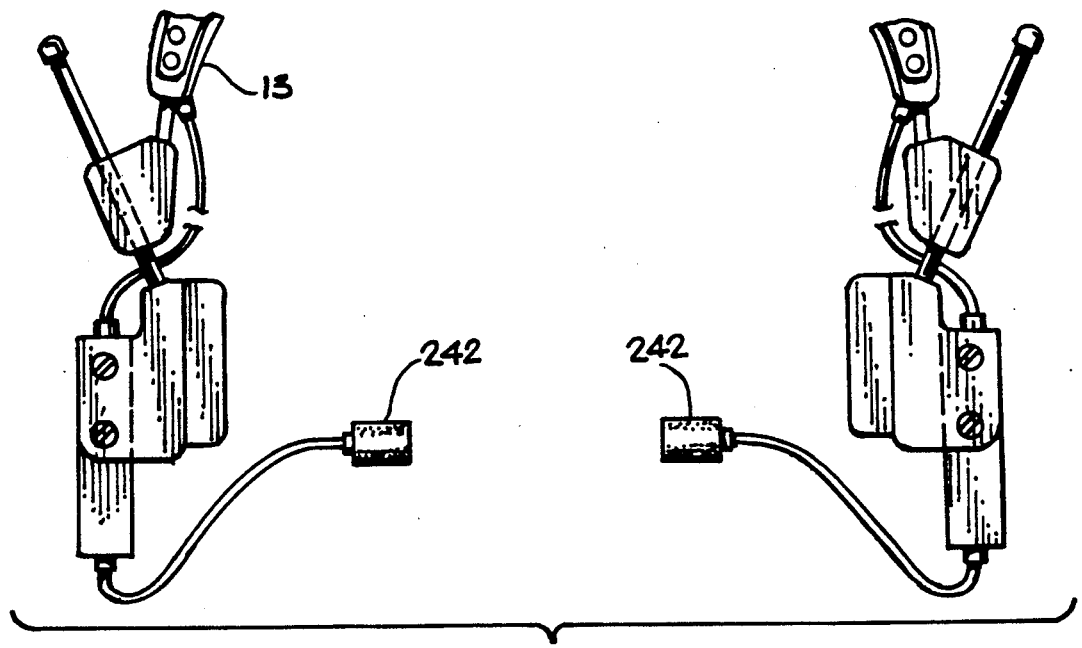
Fig.10
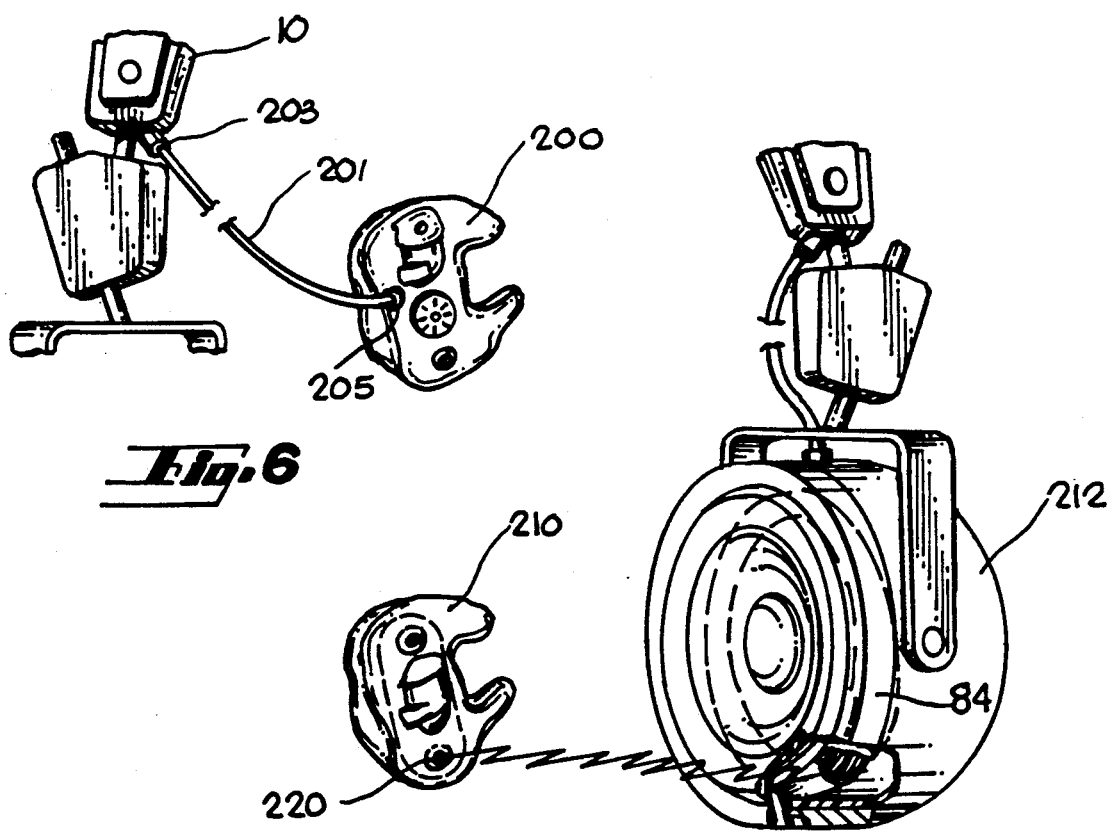
Fig.6
Fig.7

HEADSET HEARING TESTER AND HEARING AID PROGRAMMER

DESCRIPTION

1. Technical Field

The present invention relates to the field of portable hearing evaluation instruments and hearing aid programming instruments.

2. Background Art

The use of audiometric instruments in the screening and characterizing of human hearing is commonly found in schools, clinics, and in the offices of hearing aid dispensing professionals. Audiometric instruments employ pure tones, speech, and other stimuli that are within the audible range of human hearing. These sounds are delivered to the ear vicinity through transducers that are attached to the output portion of the audiometry instrument via cables.

Sound can be delivered to the ear by air-conduction transducers, such as supra-aural earphones housed in headsets, through bone-conduction transducers which make direct contact with the temporal bone area located immediately behind the ear, or by other means. Specifications and calibration standards for audiometers are available from agencies such as the American National Standards Institute (ANSI) which also provide a basis for classifications of audiometry instruments.

Recently available computer-based audiometric instruments are employed to facilitate testing procedures and improve patient records management. Automatic audiometers are becoming widely accepted in hearing screening applications such as in schools and industrial clinics. This automated process approach results in minimal operator involvement, faster testing, and in some instances improved accuracy.

Portable versions of automatic audiometry instruments incorporate microprocessors and miniature electronic components with innovative packaging and manufacturing technology to produce compact and light weight instruments suitable for most portable applications. While the cost and size of electronic components continue to decline, audiometry instruments still have at least two basic system components: a desk top electronic module connected via a cable to a separate standardized headset module to be worn on the patient's head.

Slavin, U.S. Pat. No. 4,489,610, discloses the major elements of a computerized audiometer which may be operated automatically or by a technician. The device is housed in a cabinet which contains keyboard, printer and display devices. The apparatus disclosed also includes tone generator circuits, tape recorder based audible instruction generator, central processing unit, Read Only Memory (ROM) for storage of software, Random Access Memory (RAM) for storage of diagnostic data, and further includes a programming output port for coupling to a programmable hearing aid. Other options include interface ports to connect with a modem, remote printer, and data storage devices. Similar to all other audiometry instruments, the Slavin computerized audiometer has a patient operated switch in addition to cable connected transducers (headset) to be worn by the patient.

Besserman, U.S. Pat. No. 4,284,847, discloses an audiometry apparatus which is microprocessor-based. The apparatus includes tone generation means with variable frequency and intensities, various memory elements for software and patient data storage, a key-board, and a display device. The apparatus has interface capabilities with remote computers for data transfer. One of the main features of the invention is the ability to compare recent audiogram data with previously acquired ones and automatically compute hearing threshold shifts.

U.S. Pat. No. 4,157,456 to Voss discloses an audiometric testing system having earphones, a patient feedback switch, a tone generation means which is controlled for both frequency and loudness, a memory for storage of diagnostic data, and data output means.

Voroba et al., U.S. Pat. No. 4,759,070, teach a patient controlled hearing test instrument with hearingaid programming capabilities. The system referred to as "master hearing aid" has both an operator patient's console. Both consoles are microprocessor based. The patient is presented with stimuli and using the provided console which is electrically attached to a patient-worn hearing aid via a cable, the patient can optimize hearing aid characteristics in terms of amplification and other performance characteristics. The system comprises a number of physical units, including four loudspeakers for environmental noise simulation. All units are interconnected by means of cabling. The stimuli are generated by standard tone generators, tape recorded background sounds, and verbal instructions to the patient.

U.S. Pat. No. 4,989,251 to Mangold teaches a hearing aid programming method, and U.S. Pat. No. 4,961,230 to Rising teaches a hearing aid programming interface method having a battery compartment adapted to hold a coupler member for connection to an external programming device.

It is well known in the hearing diagnostic field that even though improvements in the reliability of transducer cabling continues, damage to the cabling and contact terminals remains to be a major problem. This failure leads to intermittent dysfunction which may lead to noisy and erratic sound transmission and possibly erroneous patient diagnosis. Even if the cabling damage is promptly detected, the audiometer must remain inoperable until a replacement or a repaired headset arrives.

Another disadvantage of the cabling associated with the present two-piece audiometer systems involves the limited mobility imposed on the patient wearing the headset who must remain close to the attached base instrument. Even the most portable types of audiometry instruments presently on the market impose a penalty on both the clinician who has to provide desk space to operate or store the audiometer and the associated headset and the patient who has to deal with cables which may get tangled with other cables and instruments in the clinical setup. This is particularly problematic with active children who have the tendency to move around and displace the critical placement of the headset on the ear.

Another less obvious but very significant disadvantage of the present desk-top or lap-top audiometer approaches involves the size reduction limitation imposed by the two-piece design. Although it may seem desirable and technically conceivable to make the audiometer extremely small and light weight using very large scale integration (VLSI) technologies, functionally it is highly undesirable because of the potential for the base instrument to be pulled and moved by the headset cable as the patient moves. Not only may this motion cause the instrument to drop and possibly break but this motion will also cause mechanical movements of the instrument to become acoustically coupled to the patient resulting in interference with the on-going tests and possibly invalidating threshold measurements. For this reason, most presently available audiometry instruments must maintain a minimum size and weight to stabilize the instrument while in operation.

It is the object of this invention to provide a new approach which eliminates cabling requirements and the associated problems and allowing for a very portable and mobile operation.

It is also the object of this invention to provide an improved fitting system operation featuring automatic hearing evaluation and hearing aid programming with reduced operator intervention.

It is further the object to provide a highly flexible and modular hardware platform which is configurable by software allowing for a wide variety of clinical applications by the same instrument.

DISCLOSURE OF THE INVENTION

The above objects and others have been met with a unitary system for both testing of hearing and programming a programmable hearing aid. The system incorporates all of the necessary electronics and transducer components into a headset instrument to be worn by a patient. The headset instrument contains an electronic module with a microcontroller, a display, control switches, and interface ports for communication with external devices. A patient response device connected to the electronic module is provided for the patient to register his response to the various produced audio stimuli.

The microcontroller employs a software program via an external, plug-in, memory module which contains in addition to the program code, compressed and digitized audio data for producing various test stimuli such as pure tones, speech testing vocabulary, and operational instructions for the patient. The memory module interface is a standard Japan Electronic Industry Development Association (JEIDA) format which allows for a variety of data cards to be used, allowing for a selection among numerous memory technologies, and memory size depending on the application desired. The flexibility of compressed digital audio storage method versus traditional analog signal generators or magnetic tape-recorded mediums allow for combining both program memory and audio sources in the same solid state storage medium. Verbal instructions and test vocabulary are easily provided in different languages and accents to suit the regional needs of subjects being tested throughout the world.

The present invention also provides hearing aid fitting capabilities by computing hearing aid parameters, known as a fitting prescription, using known and published fitting formulas or algorithms, such as Prescription of Gain/Output (POGO) or National Acoustics Laboratory (NAL). These formulas use audiometry data acquired by the instrument as input for the microcontroller which applies the formula to the test data. The instrument also transfers the computed prescription to a programmable hearing aid by either direct connection methods via an electrical port or through wireless programming methods via an appropriate programming transducer device which can be among other things ultrasonic, infrared, or electromagnetic.

Thus the present invention is seen to provide highly portable, light weight, self-contained, essentially patient-operated hearing tester and hearing programmer. Such a tester-programmer instrument provides freedom of operation from the restrictions of the typically used "base-station" alternatives. The present invention, when equipped with a suitable software program, allows the user to perform testing in any area which has reasonable background noise levels such as a quiet waiting room area, patient home, school, or other quiet location.

The present invention eliminates most of the lengthy and conspicuous cable connections previously required to connect the hearing aid to the programmer instrument desk-top module or to a combined personal computer and test unit adapted to program hearing aids.

BRIEF DESCRIPTION OF THE DRAWINGS

FIG. 6 is a partial perspective view of a direct wire coupling of the apparatus of FIG. 1 to a programmable hearing aid.

FIG. 7 is a partial perspective view of an inductive wireless coupling of the apparatus of FIG. 1 to a programmable hearing aid.

FIG. 10 is a partial front view of an insert earphone module to be used with the apparatus of FIG. 1.

BEST MODE OF CARRYING OUT THE INVENTION

Figures 1, 1A:
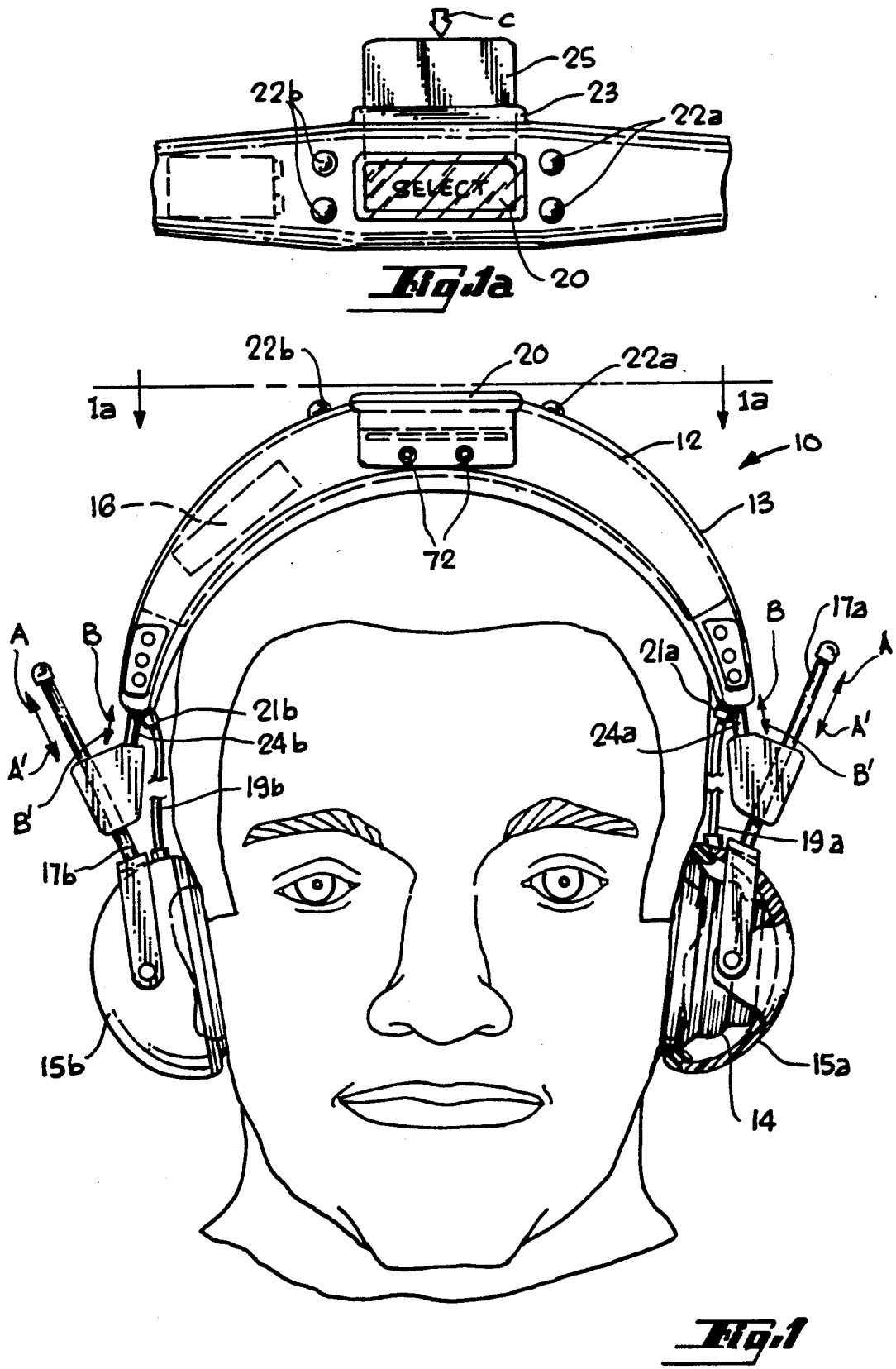
FIG. 1 is a front view of a hearing tester and programmer headset instrument in accord with the present invention.
FIG. 1a is a partial top view of the apparatus of FIG. 1, taken along lines 1a—1a in FIG. 1.
Figure 2:
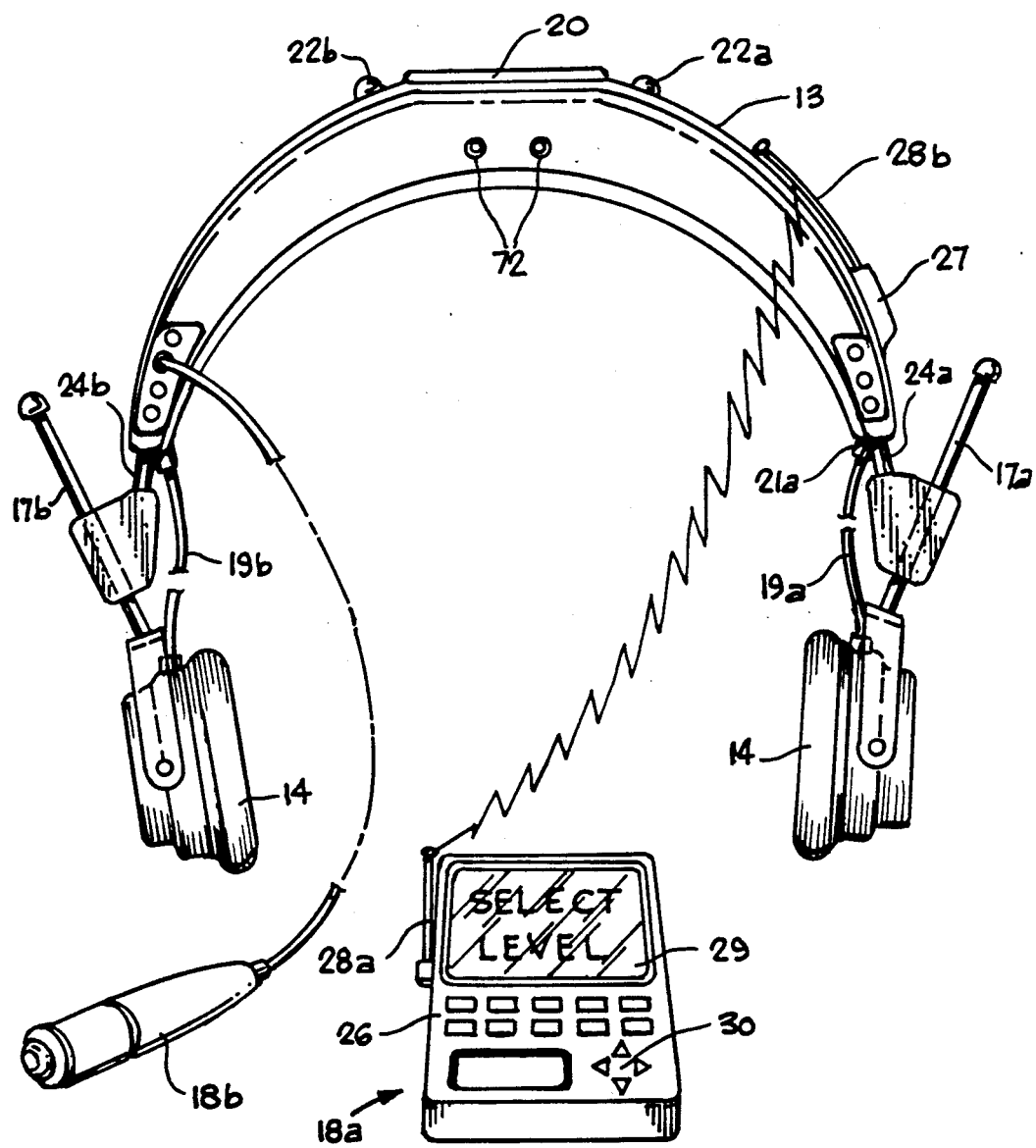
FIG. 2 is a front view of an alternative embodiment of the apparatus of FIG. 1.

With reference to FIGS. 1, 1a and 2, a self contained, patient operated hearing tester and hearing aid programmer, referred to as headset instrument 10 is shown. The instrument 10 includes an electronic assembly 12 housed in a patient-worn electronic module 13, shaped like a head-band, which has an attached acoustic transducer module 14. A battery 16 in the electronic module powers the electronic module. Battery 16 may be rechargeable. The electronic assembly 12 contains circuit boards supporting a microcontroller and peripherals described below.

The acoustic transducer module has a pair of earphones housed in optional enclosures 15a and 15b. The enclosure is used to reduce background noise while the patient is taking the test. A patient response device 18a (FIG. 2) communicates with the electronic assembly 12. The enclosures 15a and 15b are adjustably connected to electronic module 13 by rod supports 17a and 17b, movable in the direction of arrows A, A' in the usual way. The acoustic transducer module 14 is connected to the electronic assembly 12 by short wires 19a and 19b which terminate at respective ports 21a and 21b in the electronic module. The fit of the headset instrument 10 is adjustable by extension along rods 17a, 17b, 24a and 24b in the direction indicated by arrows A, A', B, and B'.

Display device 20 is provided for operator prompts. A card slot 23 receives a memory card 25 inserted in the direction of arrow C. Operator control keys 22a and 22b are used to select modes of operation from a menu described below.

Two light emitting diodes (LEDS) 72 visible to the operator are provided on the headset enclosure. They are generally used as a visual alarm to alert the operator of the status of the operation and condition of system elements. A typical application is as battery status and charging indicators. For example, a blinking red LED indicates a low battery and a blinking green LED is used to indicate that the battery is being properly charged, i.e. by good contact to a charger. Furthermore, a continuously lit green LED indicates fully charged battery.

FIG. 2 shows the acoustic transducer module without headphone enclosures 15a, 15b. Another difference in FIG. 2, relative to FIG. 1 is that a wireless link may be used as a patient response device and also to exchange data with the headset instrument. The wireless link is hand held and a patient may enter responses by means of keys 26 and observe prompts or messages on liquid crystal device (LCD) display 29, as well as hearing prompts or messages via the earphone transducer module. The wireless link includes a remote unit 18a communicating with the headset instrument via local radio frequency (RF) transceiver 27 using RF antennas 28a and 28b. Other wireless communication methods not shown are possible including optical infrared and ultrasonic communication methods. The same or a similar wireless link may be used for operator supervision, for loading or unloading data or for loading or unloading control information, or as a remote control.

In an embodiment of the present invention, which is particularly useful for pediatrics audiometry, video game methods are used to entertain the patient in order to generate and maintain interest throughout the hearing test session. One implementation of this method is to incorporate a display device 29 within the hand-held patient response device 18a as shown in FIG. 2. This display device provides visual stimulation to reinforce proper patient and instrument interaction using visual images that are interesting and challenging for children as well as adults. These images could be presented and manipulated as part of a game selected by the operator depending on the patient's age and intellectual ability. A typical display device is an LCD, chosen for low power consumption, with built-in controller such as AMD1021ST manufactured by AMD which interfaces directly to the microcontroller 32 in FIG. 3 via the address 46 and data 48 lines or indirectly via the serial I/O lines 54 with the proper serial to parallel interface within the patient response device containing the LCD. The patient response device is essentially a video game controller having directional arrow keys 30 for allowing the wireless link to be used to manipulate images, similar to a video game. Hearing test instructions and test stimuli may be combined in an entertainment format.

This play-audiometer method using a hand-held device and headset instrument elements as described above is extremely useful for children and some adults who are typically intimidated by the clinical environment. The play audiometer method is accomplished by providing the above mentioned elements which are familiar for many patients who have become accustomed to hand-held electronic games on the one hand and headphones for personal music listening on the other hand.

As an alternative to the wireless hand held response device 18a and the video game controller therein, a conventional hand operated switch 18b is connected by cable to the headset instrument. The patient response device 18a or 18b signals patient responses back to the electronics assembly 12.

Figure 3:
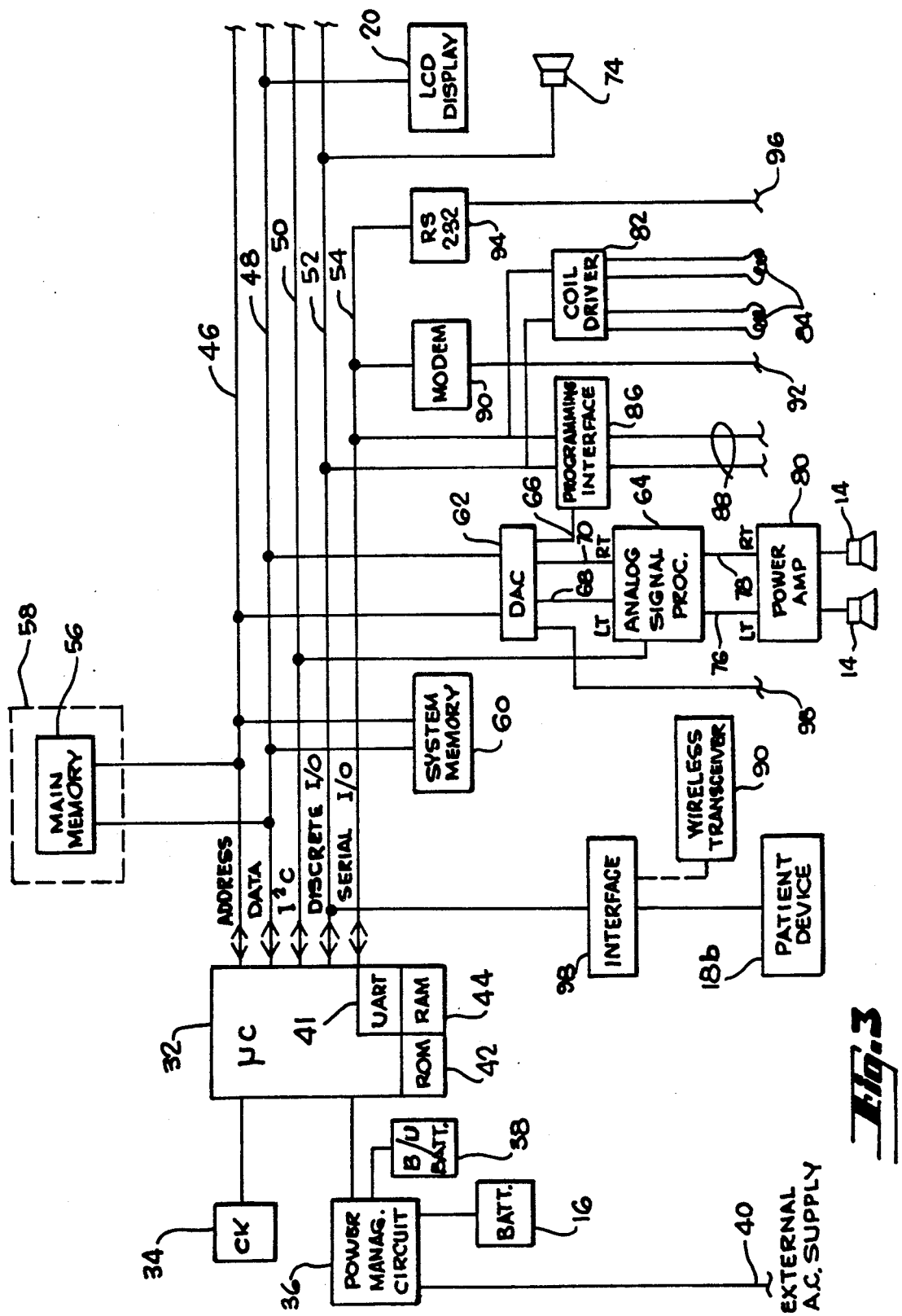
FIG. 3 is a block diagram of the electronics module employed in the apparatus of FIG. 1.

The block diagram of FIG. 3, shows the major elements of the electronic assembly of instrument 10. A central element is the microcontroller 32, such as a 83C652 manufactured by Phillips Components/Signetics. Microcontroller 32 includes 8K bytes of internal ROM 42, and 256 bytes of internal RAM 44 which is used for temporary storage of system data. Micro-controller 32 uses address bus 46, data bus 48, an inter-integrated circuit ($I^2C$) bus 50, discrete input/output (I/0) bus 52, and serial input/output (I/0) bus 54 which is implemented by a Univeral Asynchronous Receiver/-Transmitter (UART) internal to microcontroller 32.

Microcontroller 32 derives a system clock signal from clock circuits 34. System operating power is controlled by the power management circuitry 36 which turns off unused portions of the system in order to minimize power consumption. Circuitry 36 also monitors the conditions of battery 16, optionally a rechargeable battery, and signals the microcontroller when low voltage or power failures occur. Proper battery recharging is also the responsibility of the circuitry 36 which is under the control of microcontroller 32. Furthermore, circuitry 36 automatically provides backup power from a backup battery 38, in order to retain certain data when primary power is turned off or being replaced. The backup battery may be a small rechargeable cell. External power input 40 provides for connection with an external power source also capable of charging the rechargeable batteries. Although the power management circuit 36 is shown connected to microcontroller 32 only, power is supplied from the power management circuit to each functional block which requires power.

The microcontroller 32 is connected to a system random access memory, RAM 60, via address lines 46 and data lines 48. External main memory module 56, shown surrounded by dashed-line border 58, is a removable memory card, for example using a 68-pin card with compatible socket-receptacle connector. The dashed line border 58 indicates that a plurality of memory cards 56 exist. The card and connector are compatible with JEIDA standards. These main memory modules are available in a variety of capacities and types, some of which main memory modules containing a mix of both ROM and RAM. Several examples are: high density OTP-ROM, a one-time-programmable ROM, the MF42M1-G1EAT01, a 2M-byte version by Mitsubishi Electronics; a masked ROM version such as the MF72M1G1DAT01, cost effective for volume production; and the static RAM with battery backup such as the MF32M1-L2DAT01 which can be reprogrammed for software upgrades and modifications.

Generally, programs and digitized compressed audio stimuli are stored in the external main memory module 56. System RAM 60, having a typical size of 32kB-128kB, is used for data buffering and storage of various system parameters such as bank switching status, calibration data, battery status, and patient data. Internal system RAM 60 relies on memory back-up battery to retain the data while the system power is off. An example of RAM 60 is the CXK58255AP by Sony which is implemented in static CMOS technology and requires less than 2 μA at 2 volts to retain the data.

While the bulk of software programs are typically stored in external main memory 56, a smaller program will occupy the internal ROM memory 42 of microcontroller 32. This internal software can occupy up to 8K bytes of ROM 42 which is large enough to accommodate operating system code and some application programs enabling the system to operate without any external main memory 56 for simple applications requiring minimal program code such as in the case of hearing screening. However, for applications requiring substantial code memory space such as in the case of speech testing and complex hearing evaluation the external main memory 56 is required. Furthermore, the external main memory 56 provides a method of bypassing the internal program whenever needed. This is very desirable in certain situations where software modifications or upgrades are to be implemented in the field.

In order to use the external main memory 56 properly, the system must segment main memory 56 into 64K byte blocks. This is required because microcontroller 32 has maximum addressing capability of 64K bytes. However using the available discrete I/O lines to implement bank switching, a much larger memory space can be utilized.

Patient response device 18b communicates via an interface 98 to one of the several discrete I/O lines available at microcontroller 32. For electrical switches in the patient response device 18b, contact bounce removal and voltage level shifting are made within interface 98. Wireless communication between response device 18a and the electronics module requires a wireless transceiver 90 at interface 98. A similar transceiver is associated with the patient response device 18a.

Data transfer between the electronics module and other devices (computers, printers, etc.) is achieved via a miniature RS-232 interface port 96 connected to a standard RS-232 interface circuit 94. This interface circuit is connected to the serial I/O lines 54 provided by the UART section 41 of the microcontroller 32. An integrated circuit model MAX222 by MAXIM Integrated Products provides an ideal RS-232 circuit due to its low power operation and direct interface capability to the microcontroller 32.

Another data transfer method is via port 92 which is connected to a modem circuit 90. Through this port communication with remote computers via a phone line is possible. A preferred modem circuit 90 is a hybrid package model CH1776 by Cermetek Microelectronics. A liquid crystal display 20 is provided to display system options and test results for the operator. This display is connected to microcontroller 32 using the address lines 46 and data lines 48.

Audio stimuli which includes pure tones, complex sounds, background noise, speech vocabulary and verbal instructions to a patient, are digitized, compressed, and stored in the external main memory 56. When retrieved from the external main memory 56 under control of microcontroller 32 and the system software, the audio data are decompressed, processed and then provided via data bus 48 to a 4-channel 12-bit digital to analog converter ("DAC") 62, such as the MAX526 by MAXIM Integrated Products. Since the microcontroller 32 is based on an 8-bit wide data bus, 12-bit data is loaded into the DAC 62 input register using 2 write operations, 8 bits first and then 4 bits. The output of DAC 62 is an analog signal form which is appropriate for transducer input and subsequently human sound perception. Four output channels are used to provide analog signals to the left-ear and right-ear transducer channels 68, 70 for hearing testing; for generating a programmable voltage level 66 for use in a direct-wire hearing aid programming interface 86; and for a generic auxiliary output such as for use by the operator for monitoring the audio output via a miniature connector connected to port 98.

The audio analog output signals of digital to analog converter 62 are provided to the input of analog signal processor 64 whose function is to allow microcontroller 32 to independently select any one of its 4 inputs for output on either of the two audio output channel 76, 78, and to set volume, treble and bass levels. Microcontroller 32 transmits control signals and data to analog signal processor 64 using the standardized I²C bus 50. Analog signal processor 64 is a single integrated circuit such as the TDA7318D by SGS-Thompson. The treble, base and volume levels of each of its four inputs can be independently set by the microcontroller 32. Volume of the audio channels can be controlled independently in increments of 1.25 dB each.

Power amplifiers 80 receive audio outputs 76, 78 from analog signal processor 64 and provide the necessary power drive capabilities to the various audio output devices in the acoustic transducer modules 14.

Serial I/O bus 54 and discrete I/O bus 42 provide inputs to the interface circuit 86 for connection to a programmable hearing aid. For a discussion of a programmable hearing aid and a programming protocol, see U.S. Pat. No. 4,989,251 to Mangold. The data transfer during hearing aid programming is typically a serial operation. The serial communication protocol defining pulse amplitudes and durations are provided in the hearing aid manufacturer's published specifications. The DAC output 66 provides an adjustable programming voltage level to ensure compatibility with various programmable hearing aids presently on the market and future ones. Direct wire programming methods of hearing aids will be discussed below.

Buzzer 74 is provided to alert an operator of the status of a procedure or when operator intervention is required. Buzzer 74 uses I/O lines 52 which are controlled by the microcontroller 32.

In a typical situation, external main memory 56 contains the bulk of program code which is directly executable by the microcontroller 32. In addition, external memory 56 contains compressed and digitized audio data which represent pure tones, complex signals, speech vocabulary, background noise, etc. Standard compression methods perform 12-bit to 8-bit as well as 12-bit to 4-bit compression depending on the signal source type. The microcontroller will retrieve the compressed data and perform the appropriate decompression method.

The internal memory 42 typically contains initialization software in addition to basic operating system software which control the basic functionality of the system such as low level LCD control, interrupt handling routines. Furthermore, the internal memory defines the operation of the instrument 10 in the absence of external main memory 56.

Once hearing aid programming data is computed by the headset instrument, the programming data is sent to programmable hearing aids by either direct wire or wireless methods. The latter is achieved by enclosing a transmitting transducer such as an LED, a piezoelectric element, infrared, ultrasonic, or electromagnetic transmitters within the earphone enclosure. The receiving transducer is in the immediate vicinity of the transmitter, i.e. within a few centimeters. This method, as compared with existing wireless programming methods, is superior because of elimination of interfering signals by the shielding enclosure (for example, an appropriate metal enclosure will virtually eliminate electromagnetic interference). Another advantage is that the predictable alignment and close spacing between the transmitting transducer in the headset and the receiving transducer within the hearing aid leads to improved communication reliability. A further advantage is that it allows for simultaneous transmission of audio signals from transducers (earphone) and the programming signals allowing for quicker hearing aid fitting procedure. For example, speech or music signals may be produced via the earphone while a variety of hearing aid prescriptions are being sent simultaneously. The patient will select the optimal prescription based on a comparative subjective analysis. The transducer-to-transducer proximity factor provided by the configuration of the present invention enables a new implementation of a hearing aid programming method based on inductive coupling principles.

The inductive coupling method for transmitting programming data to a hearing aid is accomplished by coil driver circuit 82 and primary induction coils 84 in FIG. 3. Secondary induction coils for signal pick-up within a hearing aid will be discussed below. In an inductively coupled programming system, data is transmitted in pulses via coils 84 for reception by hearing aids equipped with a secondary coil. The pulse amplitude is controlled by DAC output 66 and pulse width duration and timing is handled by the serial I/O bus 54. DAC output 66 and I/0 buses 52 and 54 are inputs to the coil driver circuit 82.

Although programming communication typically transfers data from the headset instrument to the hearing aid, it is possible to have bidirectional communication with hearing aids equipped with sending back various information. This is particularly useful to verify that sent data has been properly received by the hearing aid.

Figure 4:
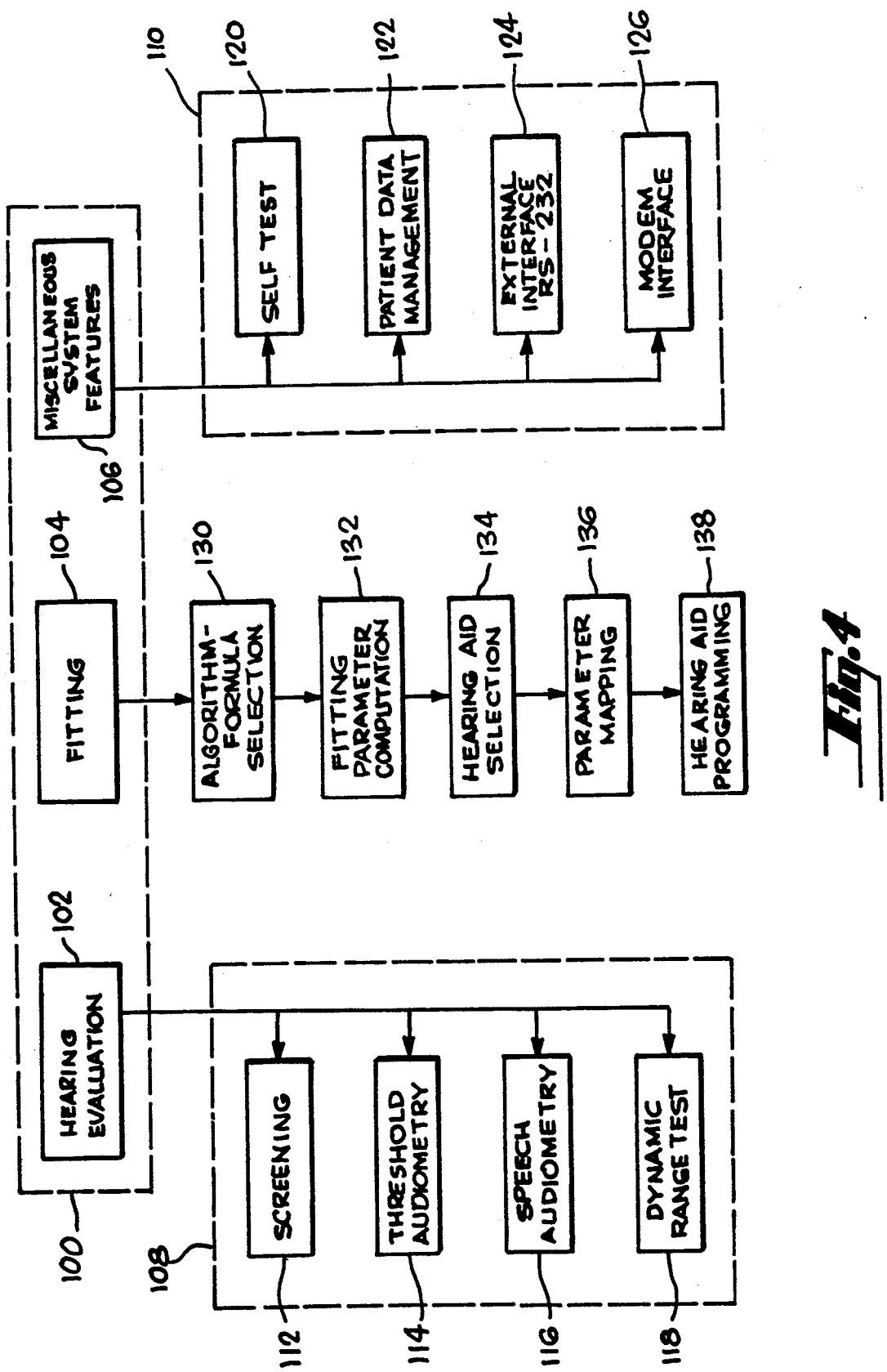
FIG. 4 is an operation diagram for a menu driven user interface used in the apparatus of FIG. 1.

FIG. 4 depicts a high level flow chart of some of the primary functions to be implemented by the headset instrument 10. Across the top of FIG. 4 are depicted a top-level menu 100 offering three choices: hearing evaluation 102, hearing aid fitting functions 104, and miscellaneous systems features 106. Selection of choice 102, hearing evaluation, results in the display on LCD 20 of menu 108. Within this second level menu are presented the following choices: screening 112, threshold audiometry 114, speech audiometry 116, or dynamic range testing 118. These hearing test methods and others not mentioned are well known by hearing evaluation professionals and are readily available for implementation by the software within the microcontroller-based instrument of the present invention.

Similarly top-level menu 100 of the hearing aid fitting option 104 leads to second-level steps 130-138. Algorithm/formula selection 130 allows the operator to select a preferred fitting method among several formulas and algorithms commonly used within the hearing aid dispensing profession. Examples include NAL (National Acoustic Laboratories) and POGO (Prescription Of Gain/Output) methods. Implementation of newer and improved methods is possible by providing an updated external memory card.

Fitting parameter computation 132 allows for the computation of hearing aid electro-acoustic parameters known as "prescription". This prescription is based on hearing test data and algorithm/formula selection 130. The prescription parameters typically include amplification requirement or gain, frequency response in addition to automatic gain control, compression ratios and other parameters provided by recently available advanced hearing aid circuits.

Hearing aid selection 134 allows the operator to display a selection of appropriate hearing aids based on the fitting parameter computation 132 and patient needs.

Once the hearing aid is selected, the electronic fitting parameters required by the hearing aid circuit are computed or mapped. These parameters allow the hearing aid to implement the electro-acoustic parameters obtained from step 132.

Finally, the mapped electronic data is transferred to the hearing aid in step 138 via any of the programming methods provided by instrument and previously discussed.

The order of steps 130 through 138 shown in FIG. 4 is a typical fitting procedure sequence for a programmable hearing aid. However, once the necessary data or selection has already been provided then any appropriate alternate procedure sequence may be performed. An attempt to perform illogical or inappropriate selection will result in the appropriate error message to be displayed and buzzer 74 to be sounded to alert the operator.

In like manner, selection of choice 106 from top-menu 100 results in display of second-level menus 110 through 126. These miscellaneous sub-menus include: self-test 120, patient data management 122, RS-232 data transfer 124, and modem communication 126.

Figure 5:
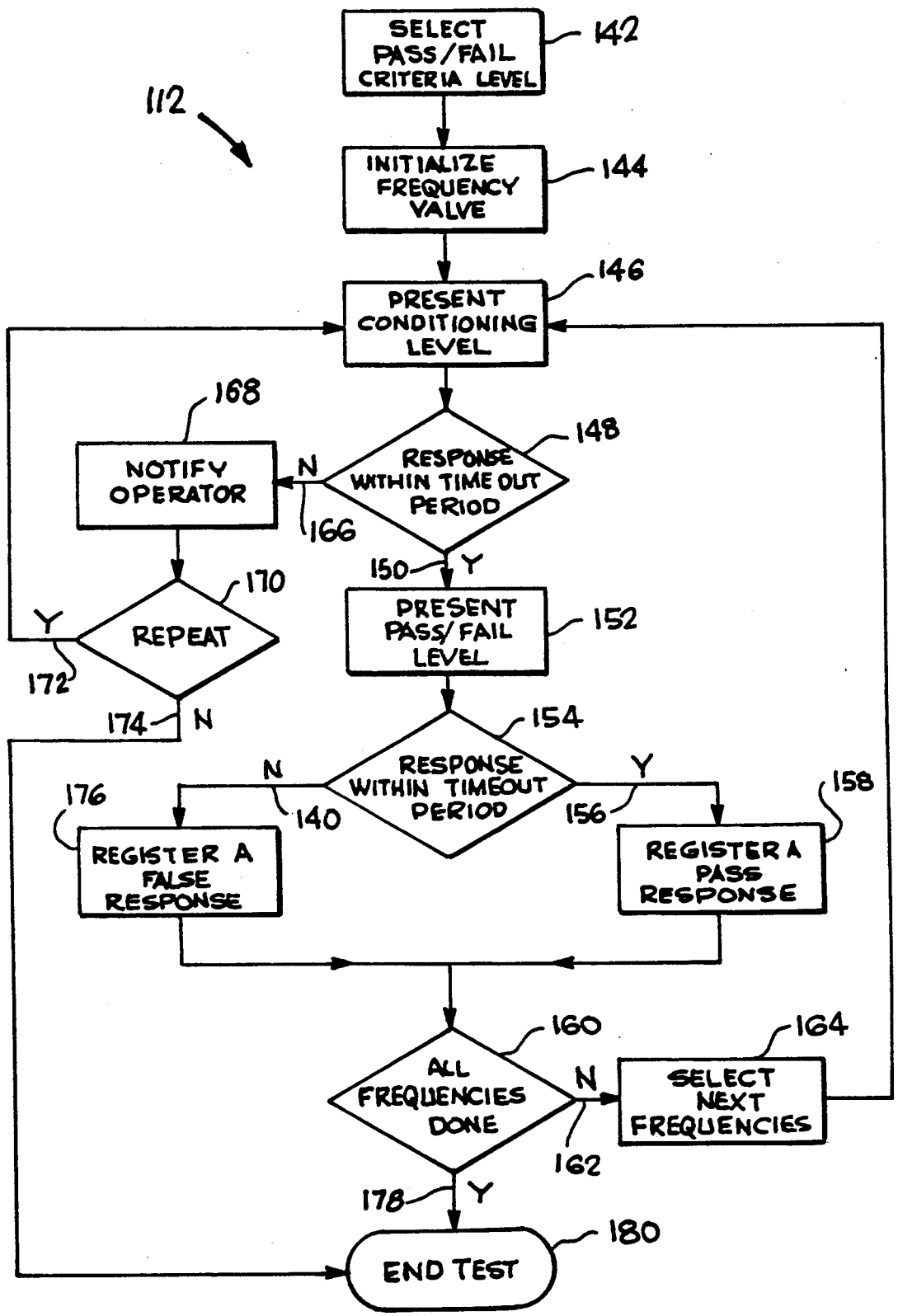
FIG. 5 is a flow diagram for hearing screening tests performed by the apparatus of FIG. 1.

FIG. 5 presents a software flow-chart diagram for a hearing screening test. A selection of the test is made by the clinician or operator from a menu displayed on the instrument display by pressing the appropriate instrument key. After instructing the patient of the basic operating principles, the instrument will produce further verbal instructions and conditioning signals in order to train the test subject on the proper instrument operation. Once the appropriate patient-machine interaction is established, test stimuli are produced and diagnostic data is computed based on the subjective response of the patient. Basically, a pass/fail screening test is a simple hearing test such as might be conducted in schools to identify children who suffer measurable hearing loss. The test must be quick, and the results based on a simple "pass/fail" criteria for each of pure tones presented at various standard frequencies.

Screening test 112 in FIG. 5 begins by requiring the operator to enter or default pass/fail criteria level at step 142. Similarly, the operator may enter or default an initial tone frequency value in step 144. This initial tone is presented at step 146 to the patient, assume a school child, at a predetermined sound pressure level (SPL) intended to familiarize the patient with the stimuli and the appropriate use of the patient response device. A predetermined timeout interval is commenced at step 148 during which an anticipated patient response is awaited. If the response is received, indicating the patient heard the tone and understands the use of the response device 18b of FIG. 2, a transition 150 is taken to reduce the SPL to that of the pass/fail criteria level which is presented at step 152. A second timeout is begun as the program awaits the patient response in step 154. A response within the timeout interval results in transition 156 to register a pass response, step 158. At step 160 the software checks if all frequencies have been tested. If another frequency tone has not yet been presented then the next frequency is determined at step 164 and the corresponding tone is presented at step 146. The test continues until all tones are presented and transition 178 ends the test.

If the conditioning presentation at step 146 has not resulted in a patient response 166 within the timeout interval 148, the operator is notified 168 by the buzzer 74. The child either has not heard the conditioning tone or does not understand the necessary interplay between the perceived tone and use of response device 18b. The operator can elect at step 170 to terminate the test 174, giving the child off-line instruction, or can repeat the conditioning tone 172, in which latter case the tone is presented once more 146.

A false response is registered 176 when a tone presented at the pass/fail level does not produce a patient response within the timeout interval 154. At the end of the test the operator is shown a list of frequencies with the corresponding pass/fail results.

FIG. 6 illustrates the direct wire connection of a programmable hearing aid 200 with the headset instrument 10. Connection is by way of cable 201, connector 203, and receptacle 205. The block diagram of FIG. 3 shows the direct connection via interface circuit 86 through ports 88, one for the left-ear channel and the other for the right-ear channel. Special voltage levels required by a particular manufacturer's programmable hearing aid is supplied using output 66 of the DAC 62. Thus a hearing aid programming software can configure a specific electrical interface for a specific hearing aid.

FIG. 7 illustrates a wireless inductive method of coupling of a programmable hearing aid 210 to the headset instrument 10. As hearing aid memory elements, EPROM cells for example, typically require voltages much higher than standard hearing aid battery voltages (1.3 v), an interface circuit is included with the coil assembly inside the hearing aid 210 to receive the transmitted RF pulses and separate the programming voltage from the programming data. Separate coupling is provided for both left-ear and right-ear programming. The hearing aid to be programmed is placed in the ear or within the ear canal, depending on the type of hearing aid used, the acoustic transducer enclosure 212 containing primary coil 84, programming transducer, is placed over the ear so that primary coil 84 and secondary coil 220 are in close proximity to one another, e.g. within a few centimeters, preferably less than four centimeters.

This scheme of energy transfer has been extensively employed for medical implant applications such as pacemakers, bladder control as well as cochlear implants. Although the primary application of this type of inductive coupling has been for transcutaneous power transmission, it is equally applicable in the present invention since the two coils will be separated by air and other non-magnetic materials.

The efficient energy transfer to the receiving coil and subsequently to the internal circuitry of the hearing aid could simplify programming requirement of the non-volatile memory, such as EPROM, EEPROM, NVRAM, etc. These types of memory typically require 16 volts or more for proper programming. Previous hearing aid programming methods which utilize non-volatile memory rely on chargepump circuits, internal to the hearing aid, which converts standard hearing aid battery voltage, 1.3 V, to higher voltages. The charge-pump circuitry increases the size, complexity, and cost of the hearing aid. The present invention allows for the elimination of the charge-pump circuitry. However, there will be other circuitry associated with the conversion of RF signals into signal data and programming energy. These circuits are well known in the art of RF data and power conversion. The added conversion circuitry is incorporated within the hearing aid next to or within the coil assembly.

Figure 8:
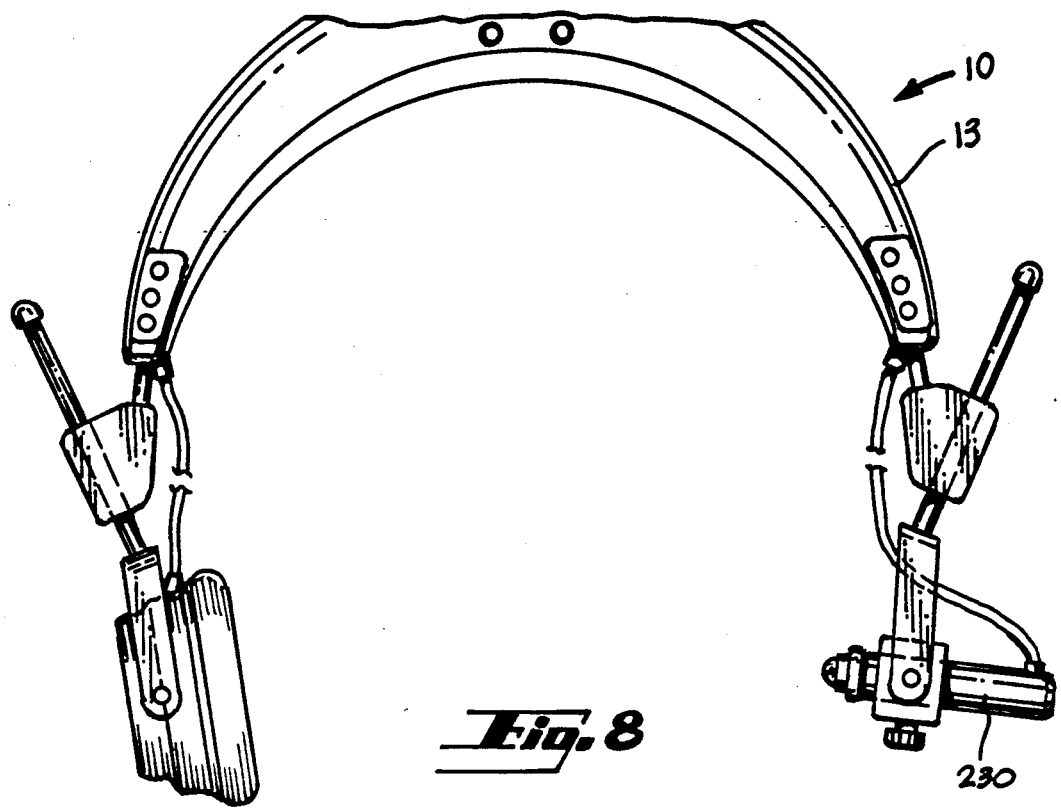
FIG. 8 is a partial front view of a tympanometry module to be used with the apparatus of FIG. 1.
Figure 9:
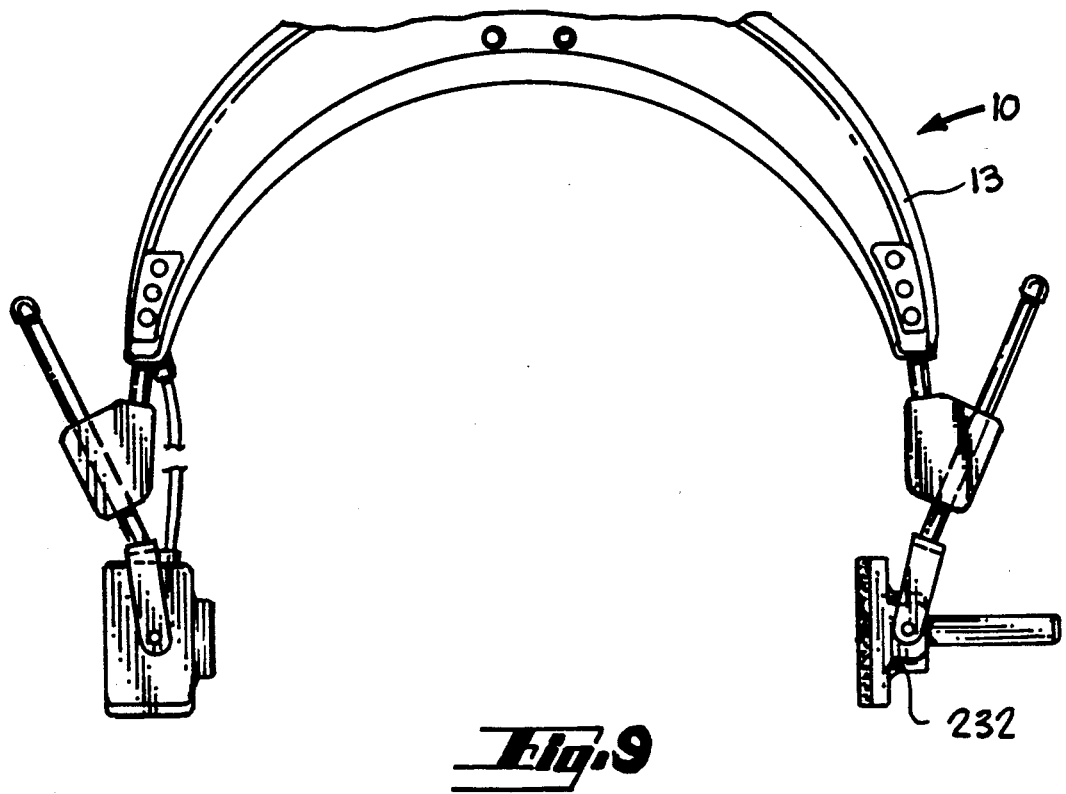
FIG. 9 is a partial front view of a bone-vibrator module to be used with the apparatus of FIG. 1.

The microprocessor-controlled headset instrument of the present invention allows for a variety of output stimulation types depending on the specific output transducer used. The headset instrument allows for modular interchange of output transducers. A variety of standard and special output devices in the acoustic transducer module can be connected to the headband associated with the electronic module. For air-conduction hearing tests for example, a standard supra-aural earphone, such as TDH39 made by Telephonics Corporation, is used as shown in FIG. 2. Alternatively, a tympanometry 230 probe could be used for acoustic impedance measurements as shown in FIG. 8. For bone conduction measurement a bone-vibrator transducer 232 is used as shown in FIG. 9. Alternatively, FIG. 10 shows an air-conduction insert earphone 242, such as ER-3A model by Etymotic Rei search, used for patients with collapsed canal problems. FIGS. 8–10 demonstrate that various output transducers can be used in the acoustic transducer module connected to electronic module 13, forming part of the headset instrument described herein.

Thus the present invention is seen to provide highly portable, light weight, self-contained, essentially patient-operated hearing tester and hearing aid programming instrument. Such a tester-programmer instrument provides freedom of operation from the restrictions of cables found in present day audiometers, while allowing programming of programmable hearing aids.

I claim:

1. A hearing tester comprising,
   a headband shaped electronic module with circuitry configured as a self-contained audiometer, with audiometer circuitry having means for producing electrical signals representing sound stimuli and means for recording a sequence of patient responses,
   acoustic transducer means mechanically connected to the electronic module for receiving said electrical signals and producing said sequence of sound stimuli, and
   a patient input signaling means connected to the audiometer for transmitting a sequence of patient responses to the audiometer.

2. The apparatus of claim 1 wherein said acoustic transducer means are removably connected to the electronic module.

3. The apparatus of claim 1 wherein said acoustic transducer means are earphones.

4. The apparatus of claim 1 wherein said acoustic transducer means are earphones within a sound enclosure.

5. The apparatus of claim 1 wherein said acoustic transducer means are bone vibrators.

6. The apparatus of claim 1 wherein said acoustic transducer means are impedance probes.

7. The of claim 1 wherein said acoustic transducer means are insertion earphones.

8. The apparatus of claim 1 wherein said electronic module accepts a data card having memory storage elements.

9. The apparatus of claim 8 wherein said data card contains digital audio test stimuli.

10. The apparatus of claim 1 wherein said audiometer has a first inductive loop means for transmitting electromagnetic signals and a second inductive loop means for receiving said electromagnetic signals at a spaced apart location.

11. The apparatus of claim 10 wherein said second inductive loop means is connected for supplying programming signals to a hearing aid.

12. The apparatus of claim 10 wherein said first inductive loop means is mounted in an enclosure.

13. The apparatus of claim 1 wherein said headband shaped module has a visual display associated therewith.

14. A hearing tester and hearing aid programmer comprising,
 a headband shaped electronic module having a microcontroller, an internal memory and a main memory, the main memory being a data card having stored digital test stimuli, and means for converting said stored digital test stimuli to audio signals,
 sound transducer means supported by the electronic module and electrically connected to said electronic module,
 a patient operated signaling means communicating with said electronic module to respond to a hearing test procedure,
 a hearing aid fitting computation program operating on data from said patient operated signaling means to produce hearing aid programming data, and
 short range transmitting means for transmitting the hearing aid programming data to a receiver associated with a programmable hearing aid.

15. The apparatus of claim 14 wherein said short range transmitting means comprises a first coil inductively coupled to a second coil spaced in close proximity to the first coil, the second coil being part of said receiver.

16. The apparatus of claim 15 wherein said first coil is mounted in an enclosure of a sound transducer.

17. The apparatus of claim 14 wherein said electronic module contains a video.

18. The apparatus of claim 14 wherein the patient operated signaling means is a video game controller.

19. A method of testing hearing of a patient and programming a hearing aid comprising,
 testing a patient with audio stimuli from an acoustic transducer and microcontroller worn by the patient,
 recording patient responses to the stimuli using said microcontroller to control recording of responses,
 transforming said responses to programmable hearing aid input data using said microcontroller, and
 transmitting said hearing aid input data over a distance of less than 20 centimeters from the vicinity of the microcontroller to the programmable hearing aid.

* * * * *